United States Patent [19]

Curbow et al.

[11] Patent Number: 4,671,307
[45] Date of Patent: Jun. 9, 1987

[54] FLOSSER

[76] Inventors: James M. Curbow; George Spector, both of 233 Broadway RM 3615, both of New York, N.Y. 10007

[21] Appl. No.: 755,159

[22] Filed: Jul. 15, 1985

[51] Int. Cl.⁴ ............................................. A61C 15/00
[52] U.S. Cl. ......................................... 132/91; 132/89
[58] Field of Search ..................... 132/91, 92 R, 92 A, 132/93, 89, 90

[56] References Cited

U.S. PATENT DOCUMENTS

| | | | |
|---|---|---|---|
| 725,462 | 4/1903 | Luallen | 132/92 A |
| 1,306,998 | 6/1919 | Dimitroff | 132/92 A |
| 1,464,013 | 8/1923 | Roberts | 132/92 A |
| 1,512,633 | 10/1924 | Peckham | 132/92 A |
| 1,952,358 | 3/1934 | Bohm | 132/92 R |
| 2,444,638 | 7/1948 | Dobbins | 132/92 R |
| 2,463,660 | 3/1949 | Turenchalk et al. | 132/91 |
| 2,577,597 | 12/1951 | Wright et al. | 132/92 R |
| 4,002,183 | 1/1977 | Restall | 132/91 |
| 4,005,721 | 2/1977 | Yasumoto | 132/91 |

FOREIGN PATENT DOCUMENTS

| | | | |
|---|---|---|---|
| 635201 | 12/1927 | France | 132/91 |
| 2007982 | 5/1979 | United Kingdom | 132/91 |

Primary Examiner—John J. Wilson

[57] ABSTRACT

A dental floss holder is provided and consists of a first C-shaped floss holding head disposed at one end of a handle at a right angle and a second C-shaped floss holding head disposed at other end of the handle colinearly. The heads are inclined at 30 degrees with respect to the plane of the handle. The first head is used to floss between back teeth while the second head is used to floss between front teeth. In a second embodiment the dental floss holder includes an H-shaped telescopic floss holding head that is angular adjustable and a handle that is length adjustable.

2 Claims, 6 Drawing Figures

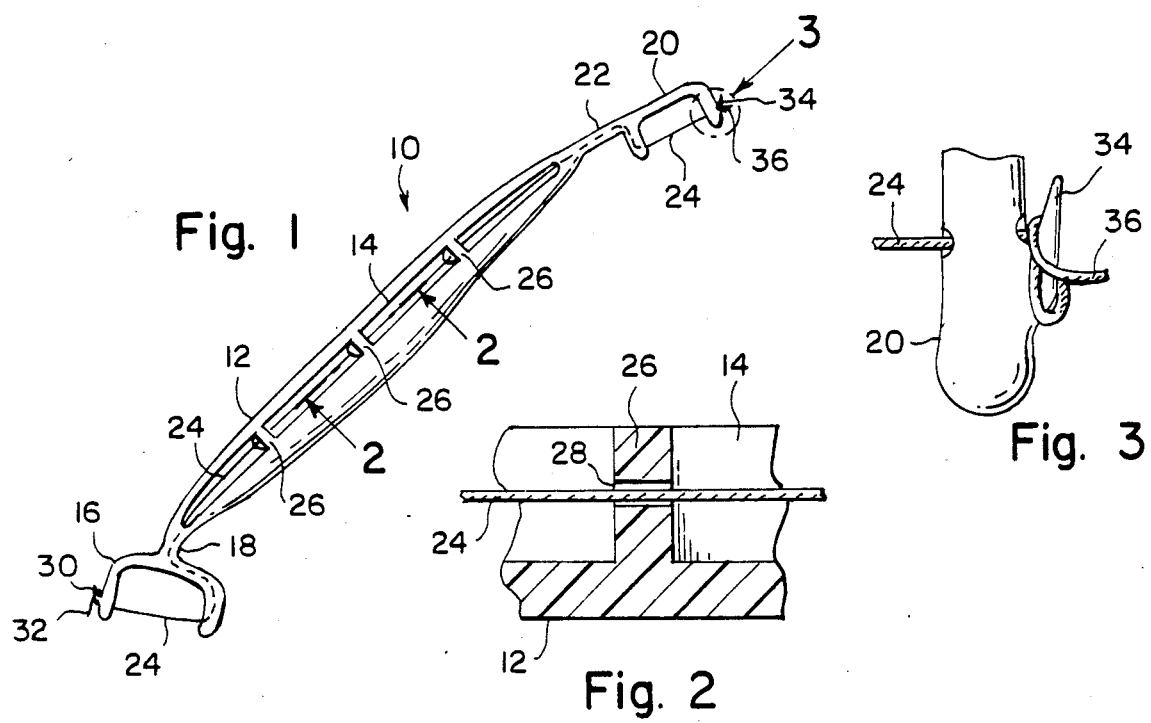
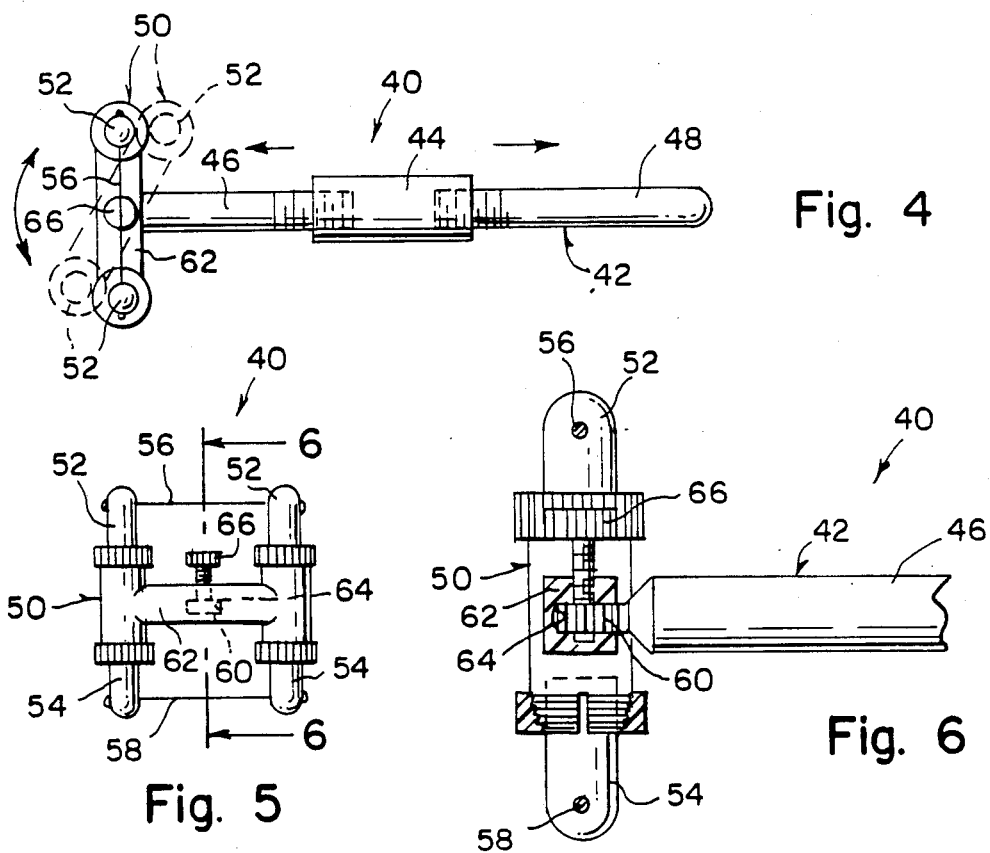

FLOSSER

BACKGROUND OF THE INVENTION

The instant invention relates generally to dental devices and more specifically it relates to a dental floss holder.

Numerous dental devices have been provided in prior art that are adapted to remove plaque from the teeth of a user. For example, U.S. Pat. Nos. 3,387,615; 4,002,183 and 4,051,857 all are illustrative of such prior art. While these units may be suitable for the particular purpose to which they address, they would not be as suitable for the purposes of the present invention as heretofore described.

SUMMARY OF THE INVENTION

A principle object of the present invention is to provide a dental floss holder that is able to floss all the teeth very easily without having to try and stretch the mouth and place the fingers within.

Another object is to provide a dental floss holder in which the dental floss is readily strung, cut, positioned and easily removed after usage.

An additional object is to provide a. dental floss holder that is adjustable to be accessable in a variety of interdental locations within the mouth.

A further object is to provide a dental floss holder that is economical in cost to manufacture.

A still further object is to provide a dental floss holder that is simple and easy to use.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 1 is a perspective view of the invention.

FIG. 2 is an enlarged cross sectional view taken along line 2—2 in FIG. 1 showing the floss track within the handle.

FIG. 3 is an enlarged detail view as indicated by numeral 3 in FIG. 1 showing one of the knife clip members which cuts the floss.

FIG. 4 is a top view of a modified dental floss holder whereby the floss holding head is angular adjustable and the handle is length adjustable.

FIG. 5 is an end view of the floss holding head showing an H-shaped configuration thereon and being telescopic.

FIG. 6 is an enlarged cross sectional view taken along line 6—6 in FIG. 5 showing the adjustment feature of the telescopic H-shaped floss head.

DETAILED DESCRIPTION OF THE PREFERRED EMBODIMENTS

Turning now descriptively to the drawings, in which similar reference characters denote similar elements throughout the several views, FIG. 1 illustrates a dental floss holder 10. An elongated handle 12 is adapted for grasping and has an exposed floss track 14 along plane of the handle 12.

A first C-shaped floss holding head 16 is disposed at one end 18 of the handle 12 at a substantially right angle and is inclined at substantially 30 degrees with respect to the plane of the handle 12. It is used to floss between back teeth of a user of the holder 10.

A second C-shaped floss holding head 20 is disposed at other end 22 of the handle 12 substantially colinearly and is inclined at substantially 30 degrees with respect to the plane of the handle 12. It is used to floss between front teeth of the user of the holder 10.

A strip of dental floss 24 is releasably affixed to the first C-shaped floss holding head 16 and extends substantially tautly therebetween. The dental floss 24 extends through the floss track 14 and is releasably affixed to the second C-shaped floss holding head 20 and extends substantially tautly therebetween.

The elongated handle 12 has a plurality of wall dividers 26 within the floss track 14 in spaced relationship. Each wall divider 26, as best shown in FIG. 2, has an aperture 28 therethrough along the plane of the handle 12 so that the strip of dental floss 24 will be held in position within the floss track 14.

The dental floss holder 10 further contains a first knife clip member 30 formed on the first C-shaped floss holding head 16 so that one end 32 of the strip of dental floss 24 can be cut and secured thereto. A second knife clip member 34 is formed on the second C-shaped floss holding head 20 so that the other end 36 of the strip of dental floss 24 can be cut and secured thereto (see FIG. 3).

FIGS. 4 through 6 show a modified dental floss holder 40 which has a length adjustable handle 42 that includes a threaded sleeve 44 and two shaft members 46 and 48 that thread into opposite ends of the sleeve 44 for adjustment.

An H-shaped floss holding head 50 is provided and has a first pair of upper spaced arms 52, 52 and a second pair of lower spaced arms 54, 54. The head 50 can be angular oriented with respect to plane of the handle 42 as shown in dotted position in FIG. 4.

Dental floss 56 is releasably affixed to the first pair of upper spaced arms 52, 52 of the H-shaped floss holding head 50 and extends substantially tautly therebetween. Dental floss 58 is releasably affixed to the second pair of lower spaced arms 54, 54 of the H-shaped floss holding head 50 and extends substantially tautly therebetween.

The first pair of upper spaced arms 52, 52 and the second pair of lower spaced arms 54, 54 of the H-shaped floss holding head 50 are telescopic. 52 and 54 are made telescopic by a collet and locknut arrangement as seen in the lower portion of FIG. 6.

As best seen in FIG. 6, shaft member 46 of the handle 42 has a toothed knob 60 extending outwardly along plane of the handle. The H-shaped floss holding head 50 has a cross arm 62 with a toothed slot 64 therein. The toothed knob 60 can enter and engage with the toothed slot 64 so that the H-shaped floss holding head 50 can be angular oriented in various positions.

A securement bolt 66 is transversely threaded within the cross arm 62 of the H-shaped floss holding head 50 to make contact with top of the toothed knob 60 preventing movement of the H-shaped floss holding head 50.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:
1. A dental floss holder which comprises
   (a) an elongated handle having a longitudianl axis adapted for grasping and having an exposed floss track parallel to said axis;
   (b) a first C-shaped floss holding head disposed at one end of said handle and inclined at substantially 30 degrees with respect to said longitudinal axis, used to floss between back teeth of user of said holder;
   (c) a second C-shaped floss holder head disposed at the other end of said handle substantially colinear and used to floss between front teeth of user of said holder;
   (d) a strip of dental floss releaseably affixed to said first C-shaped floss holding head extending substantially tautly therebetween extending through said floss track and releaseably affixed to said second C-shaped floss holding head extending substantially tautly therebetween, wherein said elongated handle includes a plurality of wall dividers within said floss track in spaced relationship, each said wall divider having an aperture therethrough along said longitudinal axis of said handle so that said strip of dental floss will be held in position within said floss track.
2. A dental floss holder which comprises:
   (a) a length adjustable handle along a longitudinal axis that includes a threaded sleeve and two aligned shaft members that thread into opposite ends of said sleeve for adjustment along said axis;
   (b) an H-shaped floss holding head having a first pair of parallel upper spaced arms and a second similar parallel spaced pair of lower arms;
   (c) means for angular orienting said head with respect to said longitudinal axis; and
   (d) dental floss releaseably affixed to said pair of upper spaced arms of said H-shaped floss holding head and extending substantially tautly therebetween and to said second pair of lower spaced arms of said H-shaped floss holding head and extending substantially tautly therebetween, wherein said first pair of upper spaced arms and said second pair of lower spaced arms of said H-shaped floss holding head are telescopic in a direction perpendicular to said floss, by means of a collet and lock nut arrangement provided on said holding head:
   (a) one of said shaft members of said handle having a toothed knob extending longitudinally outward of said handle;
   (b) said H-shaped floss holding head having a cross arm with a toothed slot therein so that said toothed knob can enter and engage with said toothed slot so that said H-shaped floss holding head can be angularly oriented in various positions; and
   (c) a securement bolt transversely threaded within said cross arm of said H-shaped floss holding head to make contact with top of said toothed knob preventing movement of said H-shaped floss holding head.

* * * * *